US00RE44580E

(19) United States
(12) Reissued Patent
Kang et al.

(10) Patent Number: US RE44,580 E
(45) Date of Reissued Patent: Nov. 5, 2013

(54) SURGICAL SCAFFOLD

(75) Inventors: Norbert Kang, Hemel Hempstead (GB); David Gavin, Hemel Hempstead (GB)

(73) Assignee: West Hertfordshire Hospitals NHS Trust, Hemel Hempstead (GB)

(21) Appl. No.: 13/588,786

(22) Filed: Aug. 17, 2012

Related U.S. Patent Documents

Reissue of:
(64) Patent No.: 7,799,075
Issued: Sep. 21, 2010
Appl. No.: 12/064,849
PCT Filed: Aug. 25, 2006
PCT No.: PCT/GB2006/003181
§ 371 (c)(1),
(2), (4) Date: Jun. 12, 2008
PCT Pub. No.: WO2007/023296
PCT Pub. Date: Mar. 1, 2007

(30) Foreign Application Priority Data

Aug. 26, 2005 (GB) ..... 0517499.0

(51) Int. Cl.
*A61F 2/18* (2006.01)
*A61M 29/00* (2006.01)

(52) U.S. Cl.
USPC ..... 623/10; 606/204.45

(58) Field of Classification Search
USPC ..... 623/10; 606/199, 204.45
See application file for complete search history.

(56) References Cited

U.S. PATENT DOCUMENTS

| | | | |
|---|---|---|---|
| 5,356,431 | A | 10/1994 | Pierce |
| 5,423,858 | A | 6/1995 | Bolanos et al. |
| 5,433,748 | A | 7/1995 | Wellisz |
| 5,716,405 | A | 2/1998 | Mittelman |
| 5,728,157 | A | 3/1998 | Prescott |
| 6,034,295 | A | 3/2000 | Rehberg et al. |
| 6,106,541 | A | 8/2000 | Hurbis |
| 6,322,590 | B1 | 11/2001 | Sillers et al. |
| 6,379,323 | B1 | 4/2002 | Patterson |
| 6,517,584 | B1 | 2/2003 | Lecalve |
| 6,554,861 | B2 | 4/2003 | Knox et al. |
| 6,786,930 | B2 | 9/2004 | Biscup |
| 7,368,124 | B2 | 5/2008 | Chun et al. |
| 7,972,379 | B2 | 7/2011 | Jung et al. |
| 2007/0270948 | A1 | 11/2007 | Wuh |

FOREIGN PATENT DOCUMENTS

| | | | |
|---|---|---|---|
| EP | 1475056 | | 11/2004 |
| FR | 2769493 | | 4/1999 |
| FR | 2769493 | A1 | 4/1999 |
| GB | 2401319 | | 11/2004 |
| GB | 2401319 | A | 11/2004 |
| JP | 8280722 | | 10/1996 |
| JP | 8280722 | A | 10/1996 |
| WO | 0047138 | | 8/2000 |
| WO | 03/071991 | | 9/2003 |
| WO | WO 03/071991 | A1 | 9/2003 |
| WO | 2005/117755 | | 12/2005 |

OTHER PUBLICATIONS

International Search Report, PCT/GB2006/003181, dated Jan. 15, 2007, 5 pages.

(Continued)

*Primary Examiner* — Suzette J Gherbi
(74) *Attorney, Agent, or Firm* — Senniger Powers LLP

(57) ABSTRACT

A scaffold for reshaping an ear or a nose, the scaffold being configured to be i) attached to the cartilaginous portion of an ear or ii) attached to the cartilaginous portion of a nose, wherein the scaffold is formed at least in part from a shape-memory material and/or a plastic material and is capable of transforming from a first configuration to a second, pre-programmed configuration.

22 Claims, 14 Drawing Sheets

(56) References Cited

OTHER PUBLICATIONS

Written Opinion, PCT/GB2006/003181, dated Jan. 15, 2007, 6 pages.
International Preliminary Report on Patentability , PCT/GB2006/003181, dated Mar. 6, 2008, 8 pages.
Search Report, GB0517499.0, dated Dec. 14, 2005, 1 page.
Abstract of FR2769493; Apr. 16, 1999.
Abstract of JP8280722; Oct. 29, 1996.
European Search Report, EP10193585, dated Jan. 12, 2012, 11 pages.
International Search Report, PCT/GB2006/003181, dated Jan. 1, 2007, 5 pages.
Written Opinion, PCT/GB2006/003181, dated Jan. 1, 2007, 6 pages.
International Preliminary Report on Patentability , PCT/GB2006/003181, dated Feb. 26, 2008, 8 pages.

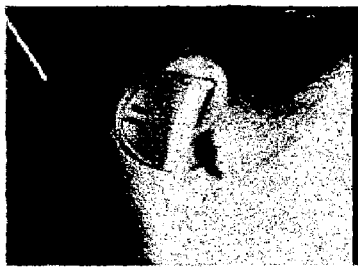
FIG. 5a
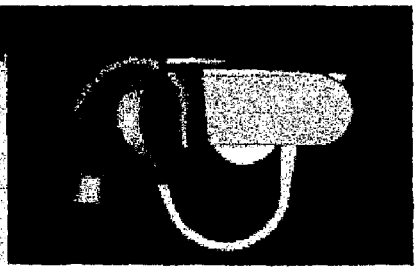
FIG. 5b
FIG. 6a
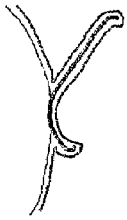
FIG. 6b
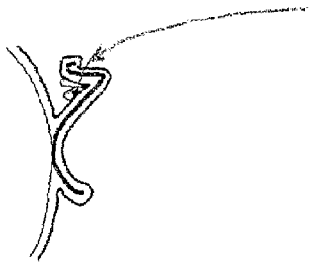
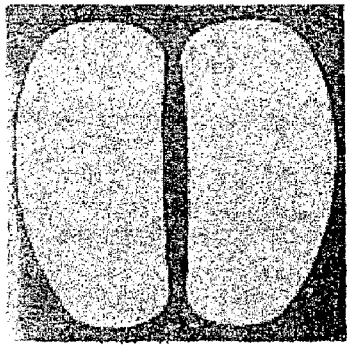
FIG. 6c

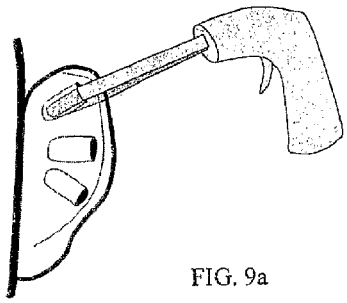
FIG. 9a
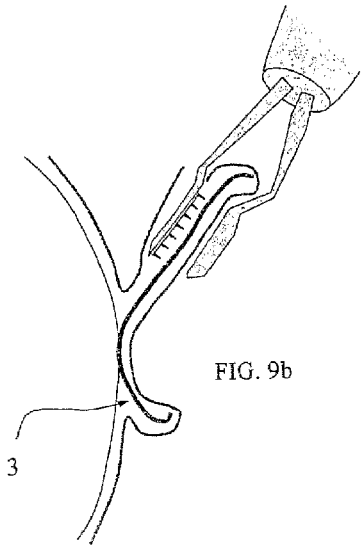
FIG. 9b
FIG. 9c
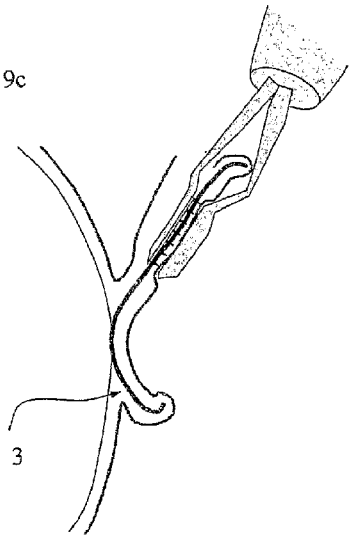
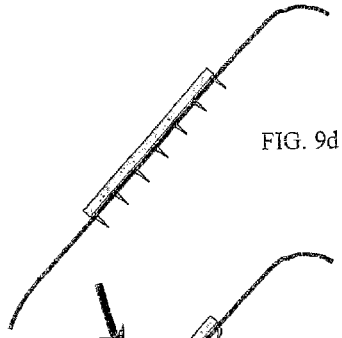
FIG. 9d
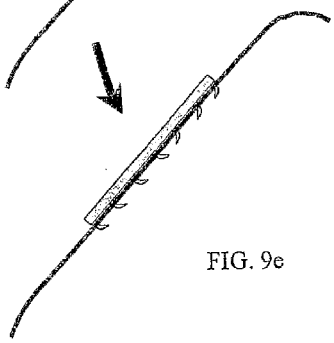
FIG. 9e

7

8

10
11
9

FIG. 12a
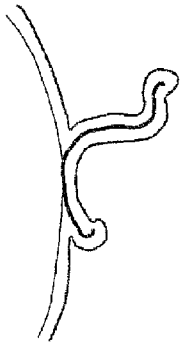
FIG. 12b
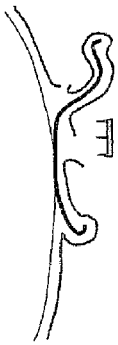
FIG. 12c
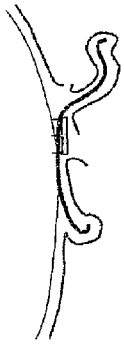
FIG. 12d
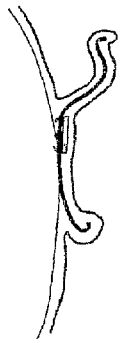
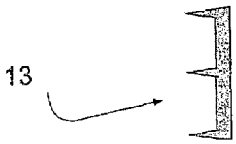
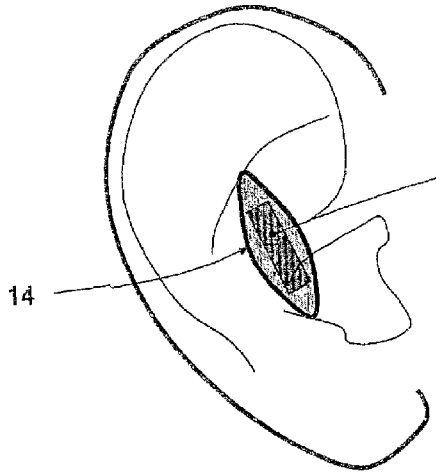
FIG. 12e

SURGICAL SCAFFOLD

Matter enclosed in heavy brackets [ ] appears in the original patent but forms no part of this reissue specification; matter printed in italics indicates the additions made by reissue.

The present invention relates to a scaffold for reshaping an ear or nose of an animal, preferably a human, wherein the scaffold is formed at least in part from a shape-memory material or a plastic material.

Prominent ear and nose deformity is common amongst the human population.

Firstly the problem of ear deformity will be considered. An ear which projects more than 17 mm from the side of the head is usually perceived as prominent. By this estimate, up to 5% of the population may be affected. Both ears are commonly affected, although occasionally just one side is prominent. The prominence may be the result of a poorly formed or absent antihelical fold (FIGS. 1 and 2). Or it may be the result of a deep conchal fossa (FIGS. 1 and 3). Alternatively, both of these abnormalities may need to be addressed when correcting prominent ears.

There are a number of known methods for addressing the problem of prominent ears. These methods may be divided into two categories, those involving otoplasy surgery (a procedure to change the shape of the ear) and those avoiding surgery. Examples of each of these categories will now be briefly discussed.

A number of operations (otoplasty surgery) are available to correct ear deformities. These vary from very invasive procedures to reshape the cartilage to minimally invasive procedures. The principle involved in all of these procedures is reshaping of the cartilage which gives the ear its prominence.

Standard, invasive, otoplasty surgery is a lengthy procedure which takes approximately 90 minutes (45 minutes for one ear). A large number of complications have been associated with this type of surgery. These include: problems with infection, bleeding, skin necrosis, death from general anaesthesia, recurrence of the prominence, keloid or hypertrophic scarring, asymmetry, palpable sharp edges (where the cartilage has been cut), pain, numbness and cold intolerance/sensitivity.

Minimally invasive otoplasty procedures (using needles or similar instruments) to reshape the cartilage have fewer complications and take less time (15 minutes for each ear), but are also less successful at achieving corrections of ear prominence. Asymmetry and palpable sharp edges are also more common compared with standard otoplasty surgery.

A further disadvantage of both standard otoplasty surgery and minimally invasive otoplasty procedures is that surgeons must undergo lengthy and costly training to learn the relevant surgical techniques. Furthermore, the results of the first 10-20 cases are likely to be unpredictable. There is currently no means by which this can be avoided.

To avoid some of the problems associated with otoplasty surgery several devices have been developed to correct prominent ears, which avoid surgery altogether.

An example of such a device is known as Earbuddies™. At birth and for a variable time afterwards (up to six months), the cartilage of the human ear remains soft and deformable. Therefore, external forces applied to the cartilage can result in permanent changes to its shape. After six months, the cartilage becomes more firm and more resistant to deformation. In the first few years of life, Earbuddies™ take advantage of the deformability of the cartilage. A piece of soft wire coated in silicone (for comfort) is moulded and placed onto the outside of the ear and taped into position (FIGS. 4a to 4c). The cartilage moulds its shape to that of the ear buddy and any prominence is corrected. More information on how the device is used is available from the website for the device at http://www.earbuddies.co.uk/pws/index.htm. Earbuddies™ are very successful when used in children up to the age of about 6 months. Thereafter, the cartilage becomes more firm and the length of time that the splint needs to remain in place to exert an effect makes it impractical to use. This is compounded by the increasing dexterity of the child who will try (and usually succeed) in removing the splint, thereby reducing its effectiveness.

An alternative device, which avoids the need for surgery is known as Auri®Clip. The Auri®Clip applies gentle, continuous, external pressure to the cartilage of the ear in the region of the antihelical fold (FIGS. 1, 5, 6). This deforms the cartilage in this area over a prolonged period of time to make the ears lie flatter against the head. The Auri®Clip forms part of the patented Auri®Method which consists of three products:

i) The Auri®Clip.

ii) The Auri®Strip, a special plaster.

iii) The Auri®Protective Spray.

According to the manufacturer, the Auri®Clip is a brace measuring 1 inch (2.5 cm) on all sides which is fixed to the ear during the night or day (FIGS. 5a and 5b). It consists of three parts: the part behind the ear, the part in front of the ear, and a lock. The Auri®Strip is a very thin (0.2 mm thick), transparent and double-sided medical adhesive material that is invisible when worn and can also be used to reshape the antihelical fold (FIGS. 6a to 6c). The Auri®Protective Spray is used together with the Auri®Clip and Auri®Strip to prevent problems with skin irritation due to prolonged usage of the Auri®Clip. The makers claim that 3 to 6 months treatment is enough to have a permanent effect. More information on the use of the device is available from http://www.aurimethod.com/index.htm.

This technique has the disadvantage that the clips cause skin irritation in some patients. Furthermore, correction of the deformities may not be complete.

Nose deformities are also common in the human population. Deformities of the nose include, for example, having a broad tip, bifid tip or cleft tip. Rhinoplasty (nose shaping surgery) has conventionally been used to address these deformities. Noses may be made smaller using reduction rhinoplasty, or enlarged using augmentation rhinoplasty. Such surgery usually involves separating the skin of the nose from its supporting framework of bone and cartilage. In conventional rhinoplasty both the bone and the cartilage may need to be reshaped. Bone, which forms approximately one-third of the nose, is relatively easy to reshape. In contrast, cartilage, which forms the remaining two-thirds, is relatively difficult to reshape. This is particularly true for the tip of the nose.

There are several disadvantages of conventional rhinoplasty. For example, traumatic dissection of the nose may damage nasal cartilages. There is also a risk of skin necrosis. Furthermore, asymmetry may be made worse by surgery. Cartilage grafts are often in short supply, especially in revision procedure and in cleft lip noses. Furthermore, the operations are often lengthy and the surgeon must be highly skilled. Training of a sufficiently skilled surgeon to perform rhinoplasty is time consuming and costly. Moreover, there are disadvantages of conventional rhinoplasty to the patient. The operation may be painful and there is a risk of adverse reaction, or even death due to the general anaesthetic. Furthermore, the results of surgery may be unpredictable and irregularities may be observed, particularly on the tip or dorsum. There is also a risk of recurrence of the deformity.

The present invention aims to address at least some of the problems and disadvantages of the prior art.

According to a first aspect of the present invention there is provided a scaffold for reshaping an ear or a nose, the scaffold being configured to be i) attached to the cartilaginous portion of an ear or ii) attached to the cartilaginous portion of the nose, wherein the scaffold is formed at least in part from a shape-memory material and/or a plastic material, and is capable of transforming from a first configuration to a second, pre-programmed configuration.

Preferably, the scaffold for reshaping an ear or a nose comprises a body portion and at least one engaging member for engaging the cartilaginous portion of an ear or a nose, wherein the scaffold is formed at least in part from a shape-memory material and/or a plastic material and is capable of transforming from a first configuration to a second, pre-programmed configuration.

In a second aspect, the present invention provides a method of reshaping an ear or a nose comprising providing a scaffold as described above, introducing at least part of the scaffold into an ear or a nose and altering the scaffold to cause the scaffold to transform from its first configuration to its second, pre-programmed configuration.

In a third aspect, the present invention provides an applicator for inserting the scaffold as defined herein into an ear or nose, the apparatus comprising means for releasably retaining the scaffold and means for deploying the scaffold into the ear or nose.

By the term "scaffold" as used herein is meant any biocompatible structure or framework, which may be used to reshape an ear or a nose. Preferably, upon implantation into a patient the scaffold does not adversely react with a patient.

The scaffold may be suitable for reshaping the anti-helical fold of the ear and/or for reshaping the conchal fossa of the ear.

The scaffold for reshaping an ear or nose may comprise a body portion and at least one engaging member for engaging in the cartilaginous portion of an ear or for engaging in the cartilaginous portion of a nose, respectively.

The body portion of the scaffold for reshaping an ear or a nose may have the shape or substantially the shape of a rectangle, a square, a rhombohedra, a circle, or another regular or irregular polyhedron. If the body portion shape has corners, it may be advantageous to round the corners or edges or otherwise alter them such that there are as few sharp corners/edges as possible. The body portion may be symmetric or asymmetric.

Preferably, the body portion of the ear scaffold will be from 0 to 35 millimeters long, from 0 to 10 millimeters wide and from 0 to 2 millimeters thick. More preferably, it will be from 5 to 25 millimeters long, from 5 to 9 millimeters wide and from 0.2 to 1.8 millimeters thick. Most preferably, it will be from 10 to 20 millimeters long, from 4 to 8 millimeters wide and from 0.5 to 1.5 millimeters thick.

Preferably, the body portion for the nose scaffold will be an irregular polyhedron.

Preferably, the body portion of the nose scaffold will have a length of from 20 to 35 millimeters, width from 0 to 15 millimeters and a thickness of from 0 to 2.5 millimeters. More preferably, the body portion for the nose scaffold will be have a length from 25 to 30 millimeters, a width of from 5 to 10 millimeters and a thickness of from 0.5 to 2.0 millimeters.

Preferably, the engaging member for engaging in the cartilaginous portion of an ear is of suitable dimensions for engaging in the cartilaginous portion of an ear, without the risk of protruding through the skin of the ear. Similarly, the engaging member for engaging in the nose will preferably be of a suitable size for engaging in the nasal cartilage, but without the risk of protruding through the skin. It will be understood by the skilled person that the suitable dimensions may vary with the size of the ear or nose in which the scaffold is to be implanted. Hence it may vary for a child and for an adult. Preferably, the engaging member has dimensions of less than, or equal to the cartilaginous portion of the ear of nose.

Preferably, the engaging members for engaging in the ear cartilage will be from 0 to 5 millimeters long and from 0 to 1.5 millimeters in diameter. More preferably, the engaging members for engaging in the ear cartilage will be from 1 to 4 millimeters long and from 0.5 to 1 millimeters in diameter.

Preferably, the engaging members for engaging in the nose cartilage will be from 0 to 5 millimeters and 0 to 1.5 millimeters. More preferably, from 1 to 4 millimeters long and from 0.5 to 1 millimeters in diameter.

The engaging members on a particular body portion may have the same length and/or width as one other engaging members on a given body portion. Alternatively, at least one engaging members may have a different length and/or width to another engaging member on a given body portion. Preferably, all engaging members on a particular body portion will all be of equal length and/or width.

The engaging members of the present invention may, for example, be in the form of spikes, prongs, tines, or cylindrical or branched protrusions. Preferably, the scaffold comprises a plurality of engaging members extending from the body portion.

The number of engaging members per body portion may be varied depending on the deformity being corrected. Preferably, the body will have at least two engaging members, more preferably it will have at least four, most preferably at least six.

The engaging members may be arranged symmetrically, or asymmetrically on the body portion.

The engaging members may all be positioned on the face of the body portion. Alternatively, at least one of the engaging members may protrude from a different face of the body portion. The engaging members may be positioned towards the edge of the body portion, or/and towards the centre of the body portion.

The scaffold for reshaping an ear or nose of the present invention may comprise a body portion without engaging members. Such a scaffold may be held in the desired position in the ear or nose by, for example, the overlying skin. It may be advantageous for a scaffold without engaging members to be used in the present invention as this may simplify application and/or removal of the scaffold to/from the ear or nose. Preferably, when the scaffold of the present invention is placed in the anterior surface of the ear, the scaffold is without engaging members.

In one embodiment of the present invention, it is advantageous for a substantial part of the body of the scaffold to have a substantially smooth surface. This allows the scaffold to be easily deployed in or removed from the nose or ear. In this embodiment it is preferable for the body not to comprise engaging members. When no engaging members are present on the scaffold it has been found to be advantageous for the body of the scaffold to have a width of less than 10 millimeters, preferably less than 5 millimeters and most preferably less than 3 millimeters. The length of the body is preferably greater than 10 millimeters, more preferably greater than 12 millimeters and most preferably less than 15 millimeters. Without wishing to be bound by any theory the present inventors have discovered that when the length of the scaffold is less than 10 millimeters and there are no engaging members, the frictional forces between the cartilage and the scaffold are not sufficient in order to allow the cartilage to grip the cartilage satisfactorily.

In a further embodiment of the present invention the body of the scaffold is designed so that the frictional contact between the scaffold and the cartilage when in place in the nose or ear is increased compared to a scaffold which has a substantially smooth surface. This may be achieved, for example, by designing the scaffold such that at least a portion of the surface of the scaffold has a rough surface. In order to ease application of such an embodiment, the scaffold may be designed so that only a portion of the scaffold has a roughened surface, and the remaining portion is smooth. Preferably the central portion of the scaffold has a roughened surface and the edge portions are substantially smooth to allow easy deployment of the scaffold into the nose or ear (see for example FIG. 18b).

Preferably the body portion of the scaffold is tapered to narrow at one end. More preferably the body portion will taper to a narrower head end, and have a wider tail end. The head end being designed to be inserted into the patient first. The tapering of the scaffold preferably decreases the lateral damage made to the skin when the scaffold is inserted or removed.

The edges of the scaffold may be straight, curved, wavy, serrated or a combination. It may be advantageous for the edges not to be straight so that the edge engages with the skin It will be understood that the scaffold for reshaping an ear or a nose may be designed to stay in the body of the patient for a substantial length of time, for example, at least two years, or more preferably at least five years. Alternatively, the scaffold may be designed to be taken out of the patient after, for example, less than two years, or less than one year, or less than six months.

The scaffold of the present invention is formed at least in part from a shape-memory material and/or a plastic material and is capable of transforming from a first configuration to a second, pre-programmed configuration.

The first and/or second configuration of the scaffold may be in a constrained or a non-constrained state. Preferably, the first configuration is in constrained state and the second configuration is in a non-constrained or vice versa.

Preferably, either the first or the second pre-programmed configuration is substantially curved and the other configuration is substantially straight.

Preferably, the first and/or second configuration of the scaffold is pre-programmed to conform to the shape of the ear or the nose. For example, it may be pre-programmed to be substantially the shape of, or at least part of the shape of, an antihelical fold, a conchal fossa, or a nasal cavity.

Preferably, the body portion and/or at least one engaging member may be formed at least in part from the shape-memory material and is capable of transforming from a first configuration to a second, pre-programmed configuration.

The term "shape-memory material" is well known in the art. As used herein the term may be defined as a material which is capable of transforming from a first configuration to a second, pre-programmed configuration. This may be initiated by a change in temperature.

The shape memory material of the present invention may be a metal alloy or a shape memory polymer.

Preferably, the alloy used is a shape memory alloy of nickel and titanium. Most preferably, the alloy comprises approximately 50% nickel and 50% titanium by weight of the total composition.

Preferably, the nickel titanium alloy used in the present invention is of the type disclosed in U.S. Pat. No. 3,174,851, which is known as "Nitinol". Details of such materials may be found is NASA Publication SP 5110 entitle "55-NITINOL"—The Alloy with a Memory, Its physical Metallurgy, Properties, and Applications, C. M. Jackson et al, 1972. Many other materials having similar characteristics are well known.

The property of nitinol which may be exploited in the present invention is the ability to pre-program a particular shape into the metal alloy and to activate the "memory" of this shape by heating/cooling it to specific temperatures. Using this property, it is possible to control the point at which the nitinol changes shape to within from 1 to 10° C., preferably within from 1 to 5° C. and most preferably within from 1-2° C. Preferably, the temperature range over which the scaffold changes from the first to the second and/or the second to the first configuration is narrow.

The scaffold of the present invention may comprise a plastic material, which may be thermoplastic. This material may be biodegradable. Furthermore, it may have shape-memory properties.

Preferably, the scaffold comprises a plastic material which is a biodegradable and/or bioabsorbable elastomer with shape memory properties. Examples of such materials may be found in Medical Device Technology, April 2005. Examples of such materials include, but are not limited to, poly(ϵ-caprolactone), or those based on crystallisable macrodiols, which may be synthesised from poly(p-dioxanone)diols and poly(ϵ-caprolactone)diol.

The scaffold of the present invention may comprise bioabsorbable or a biodegradable material, which may be a polymer or a copolymer. Examples of bioabsorbable materials which may be used in the present invention include, but are not limited to, synthetic materials such as polyacetic acid, polyglycolic acid, polydioxanone, polytrimethylene carbonate, poly(ethylene carbonate), poly(iminocarbonates), polycaprolactone, polyhydroxybutyrate, polyalkylene oxalates, polyalkylene succinates, poly(maleic acid), poly(1,3-propylene malonate), poly(ethylene terephthalate), poly(amino acids) and VICRYL™ (a bioabsorbable copolymer of glycolide and lactide). Preferably, the bioabsorbable material is a polydioxanone homopolymer. It will be understood that the selection of a suitable absorbable material will depend on such factors as the desired in vivo strength properties and absorption rate required for the scaffold.

One aspect of the present invention provides a method of reshaping an ear or a nose comprising providing a scaffold as described herein, introducing at least part of the scaffold into an ear or a nose and altering the scaffold to cause the scaffold to transform from its first configuration to its second, pre-programmed configuration.

Preferably, the present invention provides a method of reshaping an ear or a nose comprising providing a scaffold, wherein said scaffold comprises at least one engaging member as described herein, introducing at least one engaging member of the scaffold into a cartilaginous portion of an ear or a nose, and altering the scaffold to cause the scaffold to transform from its first configuration to its second, pre-programmed configuration.

Preferably, the temperature of at least some of the scaffold is altered to cause the scaffold to transform from its first configuration to its second, pre-programmed configuration. Alternatively, or additionally, force may be applied or released to the scaffold to transform the scaffold from one configuration to another.

The temperature of the scaffold may be increased or decreased to cause the scaffold to transform from its first configuration to its second, pre-programmed configuration.

It will be understood that the temperature ranges desired for transition of the scaffold from one configuration to another may be determined by the tolerance of animal/human tissue to heating and cooling, and to temperature fluctuations experienced in the nose and ear during everyday life. Preferably, the temperature of the scaffold of the present invention will remain from −20° C. to 45° C., more preferably from 0 to 42° C., most preferably, from 15 to 40° C. It is known that exposure of animal/human tissue for prolonged periods (greater than 1 minute) to temperatures above 40° C. may result in permanent damage to the tissues and prolonged exposure (hours) of the whole organism to temperatures above this level is not usually compatible with life. Similarly, exposure of animal/human tissue to prolonged periods to sub-zero temperatures is likely to damage the tissue and may lead in some cases to frost-bite. Thus prolonged exposure of the tissues to extreme temperatures is preferably avoided or minimised.

In one embodiment, wherein the scaffold comprises a body portion and at least one engaging member, the present invention provides a method comprising introducing at least one engaging member of the scaffold into the cartilaginous portion of an ear or a nose when the scaffold is at an elevated temperature, and wherein the scaffold transforms from its first configuration to its second, pre-programmed configuration as the scaffold cools below a predetermined temperature.

Preferably, the scaffold of the present invention is in a first configuration at room temperature (for example from 20 to 25° C.) and at animal/human body temperature (for example from 35 to 40° C.). This first configuration may be curved. Upon heating the scaffold above animal or human body temperature, to for example about 41 to 42° C., the scaffold transforms into a second pre-programmed configuration. The second configuration may be substantially straight. The scaffold may then be inserted into the animal or human whilst the scaffold is in its second configuration. Inserting the heated scaffold may only take a few seconds, thus tissue damage is limited. Once the scaffold has been inserted into the cartilage of the ear or nose, it may be rapidly cooled, for example, by dousing with water. Upon cooling, the scaffold is pre-programmed to transform into its first configuration and to subsequently remain in that configuration at a temperature of approximately 37° C. This may be advantageous since the mammalian bodies of particular interest to this invention usually have a temperature of approximately 35 to 40° C.

In another embodiment, the method of the present invention may further comprise manually altering the configuration of the body portion and/or at least one engaging member of the scaffold once the scaffold is positioned in the ear or in the nose.

In addition to the methods described above, the method of the present invention may further comprise altering the temperature of the scaffold to cause the scaffold to transform from its second, pre-programmed configuration to its initial configuration to allow the scaffold to be removed from the ear or from the nose.

Preferably, the shape memory material of the present invention is heated by passing an electric current through the shape memory material or by adjacent heating elements. This may permit precise control of the shape of the scaffold implant during the insertion process/reshaping process.

The method of the present invention is minimally invasive compared with standard otoplasty surgery. Thus the present invention provides a method of reshaping an ear or a nose which carries a reduced risk of complications compared to the more extensive dissection required with standard techniques. Thus, by using the method of the present invention there should be fewer problems with scarring, bleeding, skin necrosis and sharp folds in the cartilage.

It will be understood that the scaffold of the present invention can be applied quickly. It may take only 10-15 minutes to correct both ears compared with conventional otoplasty which takes up to 45 minutes for each ear.

Since the scaffold is buried under the skin and embedded in the cartilage. It does not suffer the problems encountered with poor compliance by the patient using non-surgical techniques such as Earbuddies™ or Auri®Clips.

One advantage of using the scaffold of the present invention is that the outline form of the reshaped nose or ear is highly predictable and reproducible compared to standard techniques. For example, the curvature of the antihelical fold is highly predictable and reproducible compared with standard techniques. Thus, there is less risk of problems of asymmetry compared with conventional otoplasty surgery.

It will be understood that application of the present invention will result in the immediate correction of the ear or nose deformity, unlike some methods described in the prior art, for example Earbuddies™ or Auriclip, which must be used for extended periods of time to achieve the correction desired by the patient.

Each aspect as defined above may be combined with any other aspect or aspects unless clearly indicated to the contrary. In particular any feature indicated as being preferred or advantageous may be combined with any other feature or features indicated as being preferred or advantageous.

The present invention will now be described further, by way of example, with reference to the accompanying drawings, in which:

FIGS. 5a and 5b show photographs of an Auriclip® in use and an illustration of an Auriclip®;

FIGS. 6a to 6c show an illustration of a prominent ear without and with an Auri®strip (FIGS. 6a and 6b respectively), and photograph of an Auri®strip (FIG. 6c);

FIGS. 9a to 9e show schematic illustrations of an ear scaffold of the present invention being inserted into an ear using an applicator;

FIGS. 12a to 12e show the use of the present invention to correct deep conchal fossa;

FIG. 1a shows a schematic illustration of the front view of a human ear, showing the antihelical fold (1), and the conchal fossa (2). In a normal ear the cartilage (3) of the ear normally protrudes approximately 15 to 17 mm from the skin (4) This distance is illustrated in FIG. 1b, which shows a cross-sectional view of an ear taken along the line marked X on FIG. 1a.

Figure 2A:
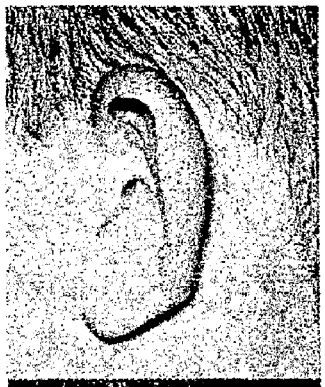
FIGS. 2a and 2b show photographs of a prominent ear due to a deformed antihelical fold before and after treatment.
Figure 2B:
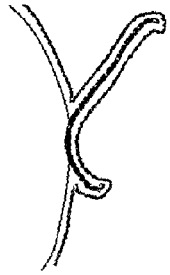
Figure 2B:
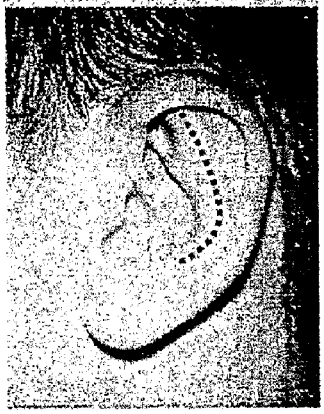

The photograph FIG. 2a shows a prominent ear due to the absence of, or a poorly formed, antihelical fold. This may be corrected by creating an antihelical fold as part of otoplasty (as shown by the dotted line in FIG. 2b).

Figure 3A:
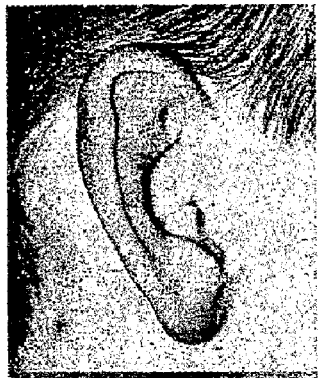
FIGS. 3a and 3b show photographs of a prominent ear due to a deep conchal fossa.
Figure 3B:
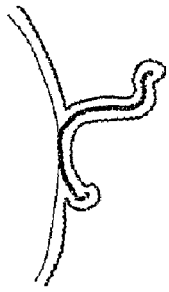
Figure 3B:
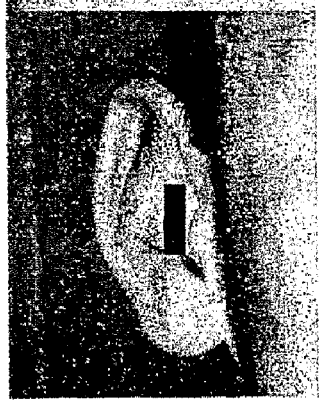

FIG. 3a shows a photograph of a prominent ear due to the presence of a deep conchal fossa. Normally, a wedge of cartilage must be removed from the ear to reduce the ear's prominence (as shown in the highlighted section of FIG. 3b).

Figure 4A:
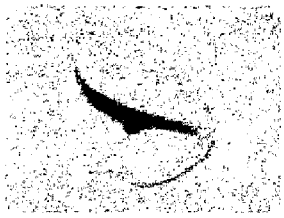
FIGS. 4a to 4c show photographs of a young child's ear before, during and after treatment with Earbuddies®.
Figure 4B:
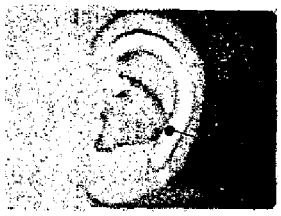
Figure 4C:
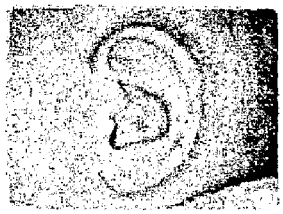

FIGS. 4a to 4c show photographs of a young child's ear before, during and after treatment with Earbuddies. FIG. 4a shows a child's ear which is prominent at birth. FIG. 4b shows an "Earbuddy"® in place in the child's ear. FIG. 4c shows the child's ear after treatment.

FIG. 5a shows a photograph of an Auriclip® in use. FIG. 5b shows a photograph of an Auriclip® in more detail. The Auriclip® has a member over which the ear cartilage is folded. The Auriclip® folds the ear cartilage by pushing the cartilage from behind.

FIG. 6a shows an illustration of an ear before treatment. FIG. 6b shows an illustration of an ear with a Auristrip® in place behind the ear creating an antihelical fold. FIG. 6c shows Auristrips® cut to size to fit behind an ear.

Figure 7A:
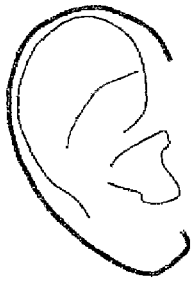
FIGS. 7a to 7c show schematic illustrations of one embodiment of the present invention being positioned in an ear.
Figure 7B:
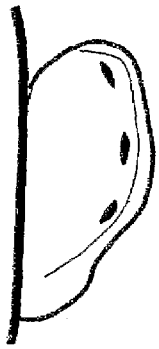
Figure 7C:
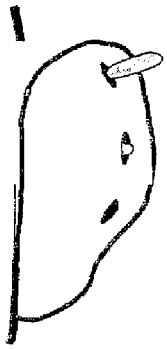

FIG. 7a shows an illustration of a prominent ear due to the absence of an antihelical fold. FIG. 7b shows three small incisions that have been made on the posterior of the skin of the ear. A small subcutaneous tunnel is made at each incision to allow the ear scaffold to be inserted. FIG. 7c illustrates the scaffolds being inserted and fixed into an ear.

Figure 8A:
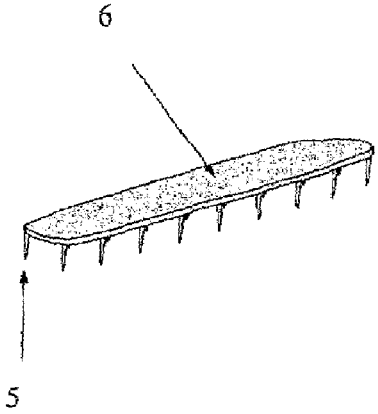
FIGS. 8a and 8b show schematic illustrations of an ear scaffold of the present invention.
Figure 8B:
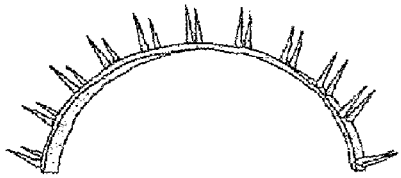

A schematic illustration of one embodiment of the scaffold of the present invention is shown in FIG. 8a. The body of the scaffold (6) may comprise nitinol (or a similar material). The body may comprise bioerodible material. Engaging members (5) may be attached to the body of the scaffold. The engaging members may be tines, or prongs to be driven into the cartilage. The scaffold may be bent into shape or may be pre-programmed to a specific degree or curvature (FIG. 8b).

FIGS. 9a to 9e illustrate one self-explanatory method of inserting the scaffold into the cartilage of an ear. The scaffold may be mounted on the tip of the applicator (FIG. 9a). The scaffold may then be deployed into the cartilage (3).

Figures 10A, 10B:
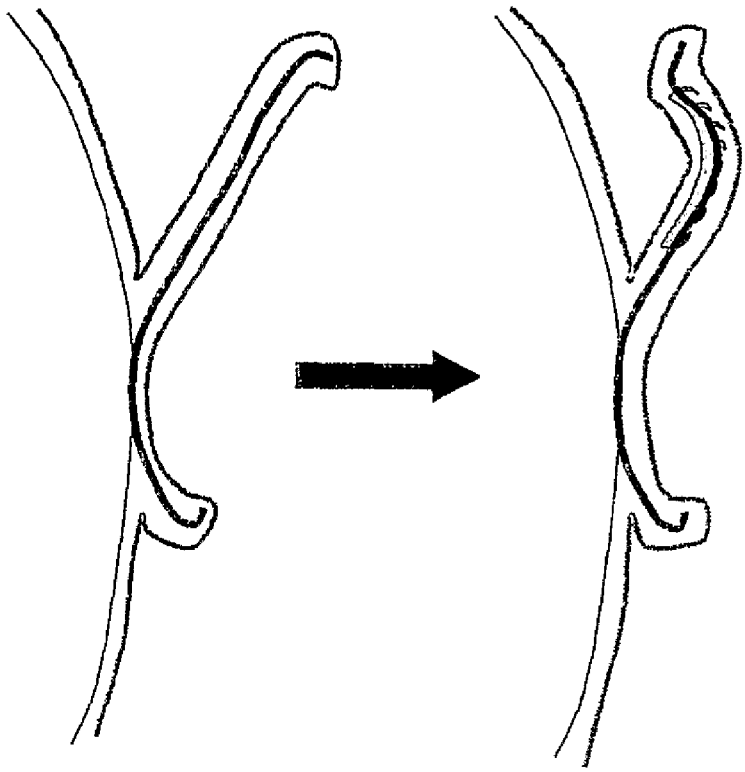
FIGS. 10a and 10b show schematic illustrations of an ear before and after insertion of a scaffold of the present invention.

FIG. 10a shows an illustration of a cross section of an ear before insertion of the scaffold. FIG. 10b shows the scaffold in place in the ear. The scaffold may be designed such that it can be bent to reshape the antihelical fold by a desired amount, or the ear staple may be pre-programmed to bend with a certain degree of curvature which may be selected before insertion.

Figures 11A, 11B, 11C:
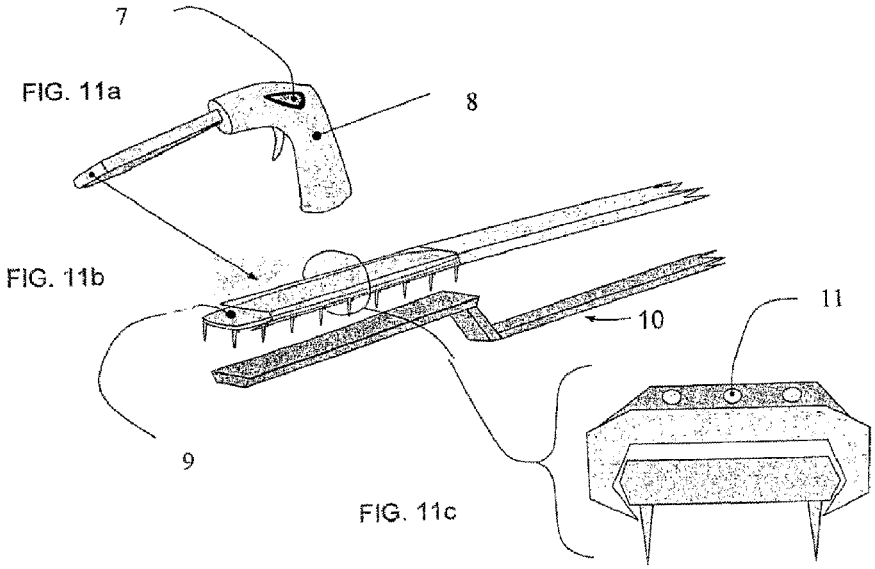
FIGS. 11a to 11c show illustrations of an applicator which may be used to insert the present invention into the patient.

FIGS. 11a to 11c illustrate an applicator which may be used to insert the scaffold of the present invention into an ear or nose. In this embodiment, the applicator (8) has a battery pack in its handle, which may be switched on to heat the scaffold via switch (7). A trigger may be used to operate the anvil which drives the ear staple into the cartilage. FIG. 11b shows an enlarged illustration of the anvil (10). The ear staple is held towards the end of the applicator (9). Advantageously the ear staple may be held straight during application to the cartilage. The applicator is then slide off allowing the ear staple to return to its curved shape upon cooling. FIG. 11c shows heating elements (11) at the tip of the applicator (8).

FIGS. 12a to 12d illustrate cross sections of an ear staple (13) being inserted into an ear to correct prominence due to deep conchal fossa. FIG. 12e shows a side view of an ear showing the scaffold in place (15) and the incision made in the conchal fossa to place the scaffold (14).

Figure 13A:
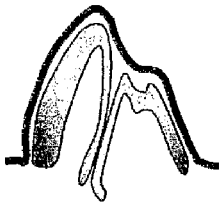
FIGS. 13a to 13d show schematic illustrations of a nose without a scaffold (FIG. 13a), with a scaffold (FIGS. 13b and 13c); and the scaffold (FIG. 13d)
Figure 13B:
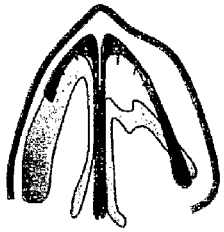
Figure 13C:
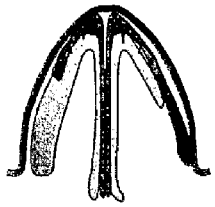
Figure 13D:
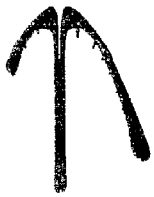

FIGS. 13a to 13d show a scaffold (FIG. 13d) of the present invention being inserted into a human nose. The skin envelope of the nose is released (FIG. 13a). The scaffold is then inserted into the nose cartilage (FIG. 13b). The scaffold may be secured in place by driving the engaging members into the cartilage. The scaffold may then be transformed into the predetermined shape (FIG. 13c). In FIG. 13c, the scaffold is secured to the alar cartilages by driving the tines (engaging members) into the cartilage. Once secure, the nasal cartilages preferably conform to the shape of the scaffold reshaping the nose.

Figure 14:
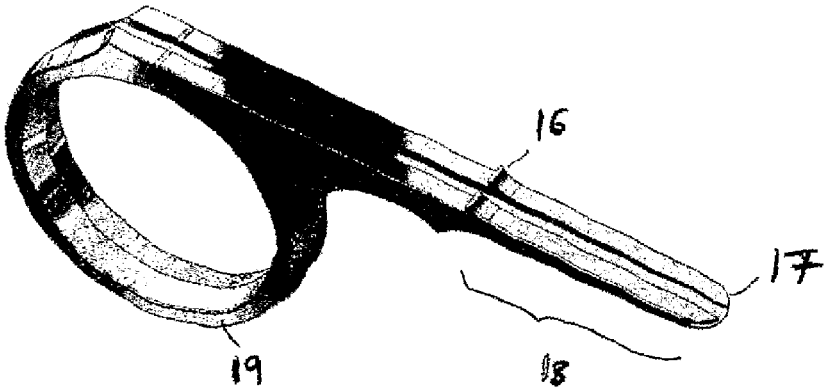
FIG. 14 shows a preferred embodiment of an applicator for the scaffold of the present invention.

FIG. 14 shows a preferred embodiment of an applicator for the scaffold of the present invention. The applicator may comprise a handle (19), a portion (18) on which the scaffold (not shown) is held prior to insertion by a retaining means (17), and a protruding section (16) which helps to position the scaffold on the applicator upon insertion to the nose or ear. The scaffold is positioned on portion (18) of the applicator prior to insertion. The portion (18) preferably holds the scaffold in the first configuration. The applicator is then inserted into a skin incision made in the ear or nose. Preferably only the portion (18) is inserted into the incision. To facilitate insertion of the applicator into the incision the applicator may be tapered towards the distal end, preferably along the portion (18) as shown in FIG. 14. The retaining means (17) may be a groove as shown in FIG. 14 into which the scaffold is designed to rest. The retaining means may be a channel for releasably retaining the scaffold. The handle (19) may be designed such that a finger may be inserted into it. Preferably the handle is designed for insertion of the middle finger. The index finger may then be used to steady the applicator.

Figure 16:
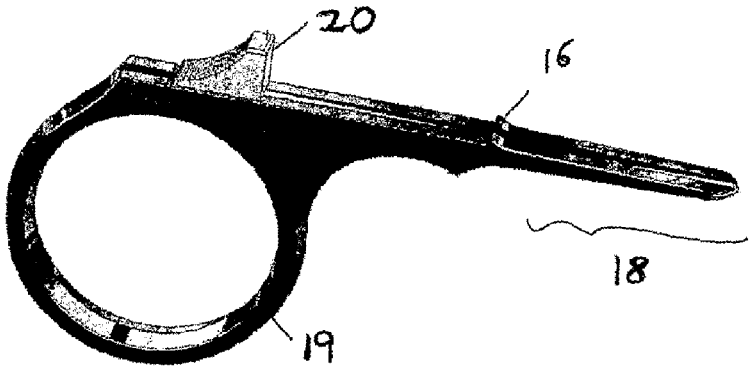
FIG. 16 shows the slider of FIG. 15 in place on an applicator, such the one shown in FIG. 14.

Preferably the applicator has stop means for stopping further deployment of portion (18) into the nose or ear. For example, the stop means may be a protruding section (16) as shown in FIG. 16.

Preferably the applicator retains the scaffold in a first configuration.

Figure 15:
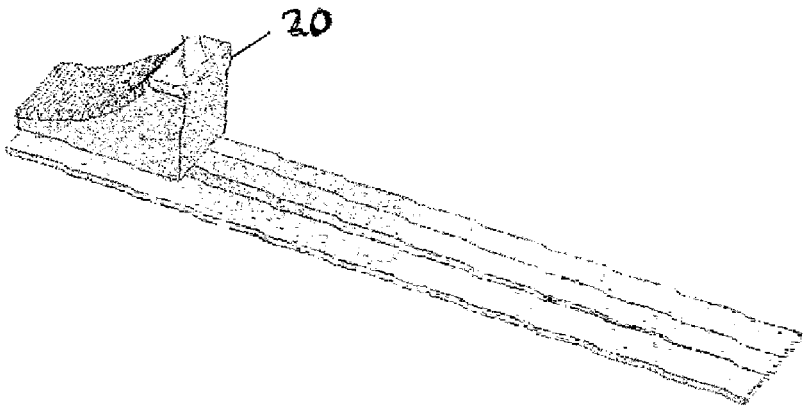
FIG. 15 shows an enlarged illustration of a slider which may form part of the applicator for a scaffold.

After the applicator has been inserted under the skin the scaffold may be deployed into position by pushing the scaffold from portion (18) of the applicator and removing the applicator from the nose or ear. The scaffold may be deployed from the applicator by means of a slider (20) (FIG. 15) which is positioned on the applicator as shown in FIG. 16. The scaffold bends into the pre-programmed shape as it is deployed from the applicator.

Figure 17:
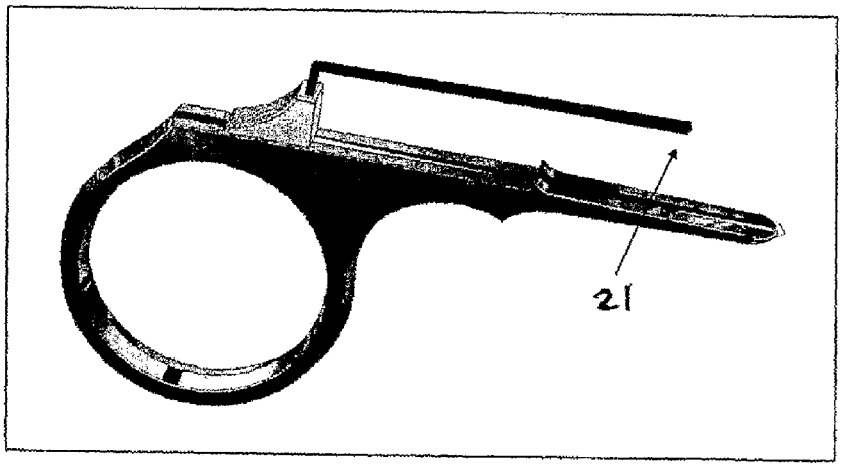
FIG. 17 shows an applicator with a locator device.

The applicator may further comprise a locator means (21) attached to the slider (20). The locator means is designed to help the operator to locate the position of the centre of the scaffold when it has been inserted under the skin. This will allow the operator to ensure that the scaffold is located directly over the middle of the antihelical fold. One example of a locator means is shown in FIG. 17.

Figure 18A:
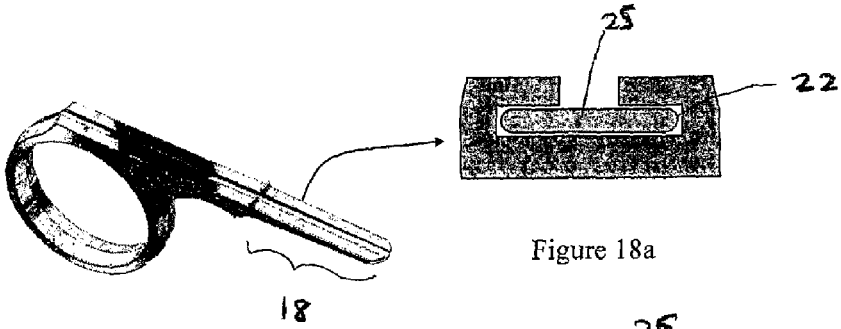
FIGS. 18a and 18b show cross-sections of portion (18) of the applicator of the present invention.

FIG. 18a shows the cross section of portion 18 of the scaffold applicator. The scaffold (25) is retained on the applicator prior to insertion in a groove (22) or channel in portion (18) of the applicator. In this example the scaffold has a substantially smooth surface so that insertion of the scaffold from the applicator is facilitated.

Figure 18B:
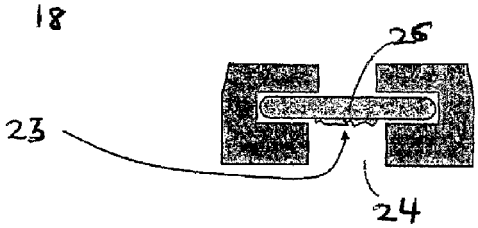

FIG. 18b shows possible alternative to the cross section of portion (18) of the applicator. In this embodiment the scaffold is designed to have a roughed surface (23) over at least some of its body. In order to ease application of such a scaffold (26), portion (18) may have a further groove (24) or channel to make space for the roughened surface (23).

Embodiment 1

Figure 1A:
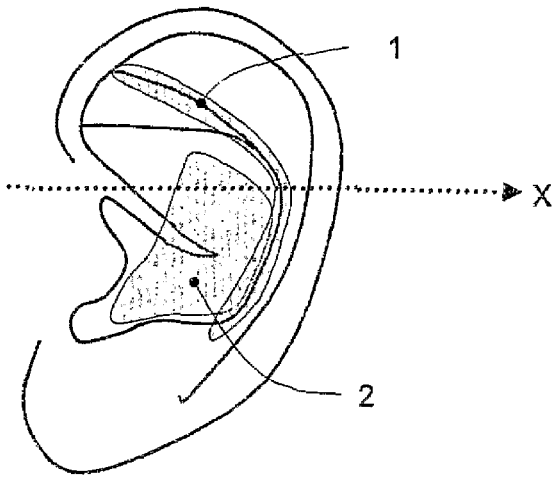
FIGS. 1a and 1b show schematic illustrations of an ear.
Figure 1B:
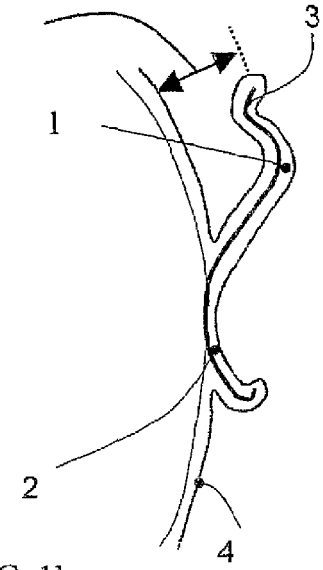

In a first example of the present invention, a scaffold is used to reshape the antihelical fold of the ear with the aim of correcting a prominent ear (see FIGS. 1a and 1b).

In this example, to change the shape of the antihelical fold, a thin strip of nitinol metal alloy (or material with similar properties) is inserted into the subcutaneous space of the skin on the posterior aspect of the ear through a small incision or series of incisions (FIGS. 7a to 7c).

The scaffold of the present invention may also be effective when placed into the subcutaneous space on the anterior aspect of the ear. However, it may be more advantageous for placement at the posterior position, because this will reduce the likelihood that the engaging member (and any incision to insert it) may become visible overtime.

In this example the scaffold is shaped with several thin "spikes", "prongs" or "tines" along its length (or just at each end) on one side of the strip (FIGS. 8a and 8b). The purpose of these spikes or tines is to allow the scaffold to be fixed securely into the cartilage of the ear.

To fix the scaffold to the cartilage, a specially designed applicator may be used to hold the scaffold in the correct position in relation to the antihelical fold of the ear (FIGS. 1a, 1b and FIGS. 9a to 9e). Once it is in the correct position (FIG. 9a), the applicator is deployed to drive the tines into the cartilage (FIG. 9b). This method may be sufficient to hold the scaffold securely (FIG. 9c). Alternatively, it may be necessary to cause the tines to curve over at their tips (FIG. 9d) to bind the scaffold more closely to the cartilage.

Once the scaffold is secured to the cartilage it is either bent into the desired shape by the user (causing the antihelical fold to be formed) or it is allowed to bend into a pre-programmed shape (FIG. 10b). The latter method allows different degrees of curvature to be pre-programmed into the invention before insertion.

The specific degree of curvature of the antihelical fold required to correct the prominence may be measured, prior to design of the scaffold. The scaffold may then be designed to specific measurements. The results of this method of correction would be highly predictable and reproducible compared with conventional techniques.

A possible applicator used to insert the invention is shown in (FIGS. 11a to 11c). The applicator may be electrically driven. This allows the shape pre-programmed into the nitinol metal alloy to be activated on command The pre-programmed shapes could include, for example, a shape where the tines are either straight or curved. The ability to control the shape of the tines would facilitate removal of the invention from the ear. This might be necessary to allow the position of the invention to be adjusted infinitely to produce the desired effect and would remove any concern about the learning curve required to produce a particular outcome.

It is anticipated that a maximum of three and a minimum of one of the scaffolds may be required to produce the desired curvature of the antihelical fold (FIGS. 7a to 7c). Once inserted, the inventions would be left in place permanently but could be removed at a later date if problems were to develop.

Embodiment 2

In a second embodiment of the present invention, a scaffold is used to correct deep conchal fossa (see FIGS. 3a, 3b and FIGS. 12a to 12e).

An incision is made in the conchal fossa to facilitate insertion of the staple (FIGS. 12b and 12e). A separate incision is made behind the ear to allow the soft tissues to be repositioned (FIG. 12b). The ear is pushed back alongside the head by the desired amount (FIG. 12b). A staple is inserted through the anterior incision which holds the ear in the desired position (FIGS. 12c and 12e). The engaging members, for example, the tines or spikes will then be made to curve over holding the staple in the correct position (FIG. 12d) as with the invention for reshaping the antihelical fold.

Embodiment 3

In the third embodiment of the present invention a scaffold is used to correct a deformed nose (see FIGS. 13a to d).

The skin envelope is released from the nose to allow reshaping of the deformed nasal cartilage. The nose scaffold used to correct the deformity, in this example, comprises two bent body portions. Each portion comprises a substantially straight part, and a curved part. The curved part comprises engaging members which may be used to engage in the cartilage of the nose.

The scaffold is inserted into the cartilage of the nasal cavity. The skin envelope is then draped over the new cartilage scaffold.

The scaffold is then secured to the alar cartilage by driving the engaging members into the cartilage. The engaging members are than heated (or they may be cooled in other embodiments of the present invention) to cause the engaging members to curve into the alar cartilage. In other embodiments of the present invention, the engaging members need to curve upon transition to a second pre-programmed configuration. Once the scaffold is in place. The nasal cartilage may conform to the new scaffold shape, giving the nose a new shape.

The invention claimed is:

1. A scaffold for reshaping an ear or a nose, the scaffold configured to be (i) attached to the cartilaginous portion of an ear or (ii) attached to the cartilaginous portion of a nose, wherein the scaffold is formed at least in part from a shape memory material and is capable of transforming from a first configuration to a second pre-programmed configuration, wherein the scaffold comprises a body portion and a plurality of engaging members in the form of prongs extending from the body portion for engaging the cartilaginous ear or nose portion.

2. A scaffold as claimed in claim 1, wherein the scaffold is transformable from said first configuration to said second configuration at a predetermined temperature or over a predetermined temperature range.

3. A scaffold as claimed in claim 1 wherein the first configuration is in a constrained state and the second configuration is in a non-constrained state.

4. A scaffold as claimed in claim 1 wherein the first configuration is in a non-constrained state and the second configuration is in a constrained state.

5. A scaffold as claimed in claim 1 wherein the first configuration is pre-programmed to conform to the shape of an ear or nose.

6. A scaffold as claimed in claim 1 wherein the second configuration is pre-programmed to conform to the shape of an ear or nose.

7. A scaffold as claimed in claim 1 wherein the first or the second configuration is substantially curved and the other configuration is substantially straight.

8. A scaffold as claimed in claim 1, wherein the body portion is formed at least in part from the shape-memory material and is capable of transforming from a first configuration to a second, pre-programmed configuration.

9. A scaffold as claimed in claim 1, wherein the at least one engaging member is formed at least in part from the shape-memory material and is capable of transforming from a first configuration to a second, pre-programmed configuration.

10. A scaffold as claimed in claim 1, which is suitable reshaping the anti-helical fold of the ear.

11. A scaffold as claimed in claim 1, which is suitable for reshaping the conchal fossa of the ear.

12. A scaffold as claimed in claim 1, wherein the shape-memory material is an alloy of nickel and titanium.

13. A method of reshaping an ear or a nose comprising providing a scaffold configured to be (i) attached to the cartilaginous portion of an ear or (ii) attached to the cartilaginous portion of a nose, wherein the scaffold is formed at least in part from a shape memory material and is capable of transforming from a first configuration to a second pre-programmed configuration, wherein the scaffold comprises a body portion and a plurality of engaging members in the form of prongs extending from the body portion for engaging the cartilaginous ear or nose portion, introducing at least part of the scaffold into an ear or a nose and altering the scaffold to cause the scaffold to transform from its first configuration to its second, pre-programmed configuration.

14. A method of reshaping an ear or a nose as claimed in claim 13, wherein at least one of said engaging members is introduced into a cartilaginous portion of an ear or a nose.

15. A method as claimed in claim 13, wherein the temperature of the scaffold is altered to cause the scaffold to transform from its first configuration to its second, pre-programmed configuration.

16. A method as claimed in claim 15, wherein the at least one engaging member of the scaffold is introduced into the cartilaginous portion of an ear or a nose when the scaffold is at an elevated temperature, and wherein the scaffold transforms from its first configuration to its second, pre-programmed configuration as the scaffold cools below a predetermined temperature.

17. A method as claimed in claim 13 which further comprises manually altering the configuration of the body portion and/or at least one engaging member of the scaffold once the scaffold is positioned in the ear.

18. A method as claimed in claim 13, which further comprises altering the temperature of the scaffold to cause the scaffold to transform from its second, pre-programmed configuration to its initial configuration to allow the scaffold to be removed from the ear.

*19. The scaffold of claim 1 in combination with an applicator for inserting the scaffold into an ear or nose, the applicator comprising the scaffold and means for releasably retaining the scaffold and means for deploying the scaffold into the ear or nose.*

*20. The scaffold of claim 19 in combination with the applicator and further comprising a handle.*

*21. The scaffold of claim 12 in combination with an applicator for inserting the scaffold into an ear or nose, the applicator comprising the scaffold and means for releasably retaining the scaffold and means for deploying the scaffold into the ear or nose.*

*22. The scaffold of claim 21 in combination with the applicator and further comprising a handle.*

* * * * *